United States Patent [19]

Sugahara et al.

[11] Patent Number: 4,519,891

[45] Date of Patent: May 28, 1985

[54] LIQUID FILM TYPE, ANION-SELECTIVE ELECTRODE

[75] Inventors: Kenshi Sugahara; Kazuo Yasuda, both of Katsuta; Junji Mori, Hitachi, all of Japan

[73] Assignee: Hitachi, Ltd., Tokyo, Japan

[21] Appl. No.: 574,587

[22] Filed: Jan. 27, 1984

[30] Foreign Application Priority Data

Jan. 28, 1983 [JP] Japan .................................. 58-13065

[51] Int. Cl.³ ............................................ G01N 27/30
[52] U.S. Cl. ................................................. 204/418
[58] Field of Search ................................. 204/418, 1 T

[56] References Cited

U.S. PATENT DOCUMENTS

| | | | |
|---|---|---|---|
| 3,840,452 | 10/1974 | Baum et al. | 204/418 |
| 4,276,141 | 6/1981 | Hawkins | 204/418 X |
| 4,349,426 | 9/1982 | Sugahara et al. | 204/418 |
| 4,379,041 | 4/1983 | Petránek et al. | 204/418 |
| 4,399,002 | 8/1983 | Freiser et al. | 204/1 T |

FOREIGN PATENT DOCUMENTS 89689 7/1979 Japan .
77952 5/1982 Japan .

Primary Examiner—G. L. Kaplan
Attorney, Agent, or Firm—Antonelli, Terry & Wands

[57] ABSTRACT

A liquid film type, anion-selective electrode of the present invention is suitable for measuring a chloride ion concentration of blood. A sensitive film contains a plurality of plasticizers having different dielectric constants, an anion-sensitive substance and a polymeric support material for supporting them. An appropriate content of o-nitrophenyloctylether having a high dielectric constant is 5–30% by weight, an appropriate content of n-tetradecyl alcohol having a low dielectric constant 5–40% by weight, and an appropriate content of dimethyldioctadecylammonium chloride as the anion-sensitive substance is 5–30% by weight. An electrode for measuring anions with such a sensitive film has less adverse affect by protein on measurements. The sensitive film further containing n-dodecyl alcohol has a much smaller error of measurement.

28 Claims, 9 Drawing Figures

N = 22
AUE1 = 104.7 +− (9.3)
AUE2 = 100.3 +− (9.3)
R = 0.9808
Y = 0.98X + (−2.61)
SYX = 1.91

N = 26
AUE1 = 105.7 +- ( 9.1)
AUE2 = 104.9 +- (11.6)
R = 0.8985
Y = 1.14X+(-15.73)
SYX = 5.30

N = 22
AUE1 = 104.7 +- ( 9.3)
AUE2 = 101.4 +- ( 9.6)
R = 0.9834
Y = 1.01X+(-4.83)
SYX = 1.83

LIQUID FILM TYPE, ANION-SELECTIVE ELECTRODE

BACKGROUND OF THE INVENTION

This invention relates to a liquid film type, anion-selective electrode, and particularly to a liquid film type, anion-selective electrode based on a polymer support film suitable for measuring inorganic anions such as a chloride ion.

Liquid film type, anion-selective electrodes are less susceptible to influences by halogen, sulfides, etc., than inorganic solid film type electrodes and have been used for measuring body liquids such as blood, urine, etc. Known typical liquid film type electrodes are anion-selective electrodes comprising a sensitive film which is based on ion exchange liquid film and which supports a quaternary ammonium salt as a sensitive substance in a synthesized polymer support of polyvinyl chloride, etc. as disclosed, for example, in U.S. Pat. No. 4,349,426.

These liquid film type electrodes have problems, when chloride ions in body fluids are to be measured, such as a large error of measurement due to influences by substances deposited on the surface of the sensitive film and a difficulty to obtain a high responsiveness. Thus, many attempts have been so far made to solve these problems. For example, Japanese Patent Application Kokai (Laid-open) No. 54-89689 proposes to use methyltridodecylammonium chloride as a sensitive substance and o-nitrophenyloctylether as a plasticizer to improve the response speed, and Japanese Patent Application Kokai (Laid-open) No. 57-77952 proposes to use methyltridodecylammonium chloride as a sensitive substance and n-tetradecyl alcohol as a plasticizer to reduce adsorption of protein, etc.

However, these proposed attempts still suffer from such problems that errors of measurement are considerably increased by improving the responsiveness, whereas the responsiveness is considerably deteriorated by improving a composition to reduce the errors of measurement. Thus, development of practically distinguished anion-selective electrodes has been keenly desired.

SUMMARY OF THE INVENTION

An object of the present invention is to provide a liquid film type, anion-selective electrode with a good responsiveness and less errors of measurement.

Another object of the present invention is to provide an anion-selective electrode with less deposition of protein when used for measuring body fluids.

Another object of the present invention is to provide an anion-selective electrode with a long life, which can produce correct results of measurement for a prolonged time.

To attain these objects, the present invention provides a sensitive film on an electrochemical electrode, the sensitive film comprising a polymer film containing a plasticizer of linear alcohol having a low dielectric constant and a plasticizer of organic compound having a high dielectric constant together with an anion-sensitive substance.

According to a preferable mode of the present invention, aliphatic alcohols having 10-20 carbon atoms and a dielectric constant of not more than 10 are used as the plasticizer of low dielectric constant. Liquid organic compounds having a high lipophilicity, a low water solubility and a dielectric constant of 15 or higher are used as the plasticizer of high dielectric constant. When the plasticizer of high dielectric constant is a cyclic compound, it preferably has at least 6 carbon atoms, and when it is an aliphatic compound, it preferably has at least 10 carbon atoms.

Quaternary ammonium salts are suitable for the anion-sensitive substance, and quaternary phosphonium salts can be also used. According to a preferable mode of the present invention, a quaternary ammonium salt has a plurality of aliphatic alkyl groups, sum total of carbon atoms of the alkyl groups being at least 32. Dimethyldialkylammonium salts with long alkyl chains are suitable for measuring chloride ions.

Polyvinyl chloride, epoxy resin, silicone resin, or cellulose resin can be used as a support film substance of the sensitive film. Polyvinyl chloride is a suitable support film substance for measuring blood samples. It is more effective to add to the sensitive film substances capable of increasing the solubility of the anion-sensitive substance and reduce the crystallization of the plasticizers. A preferable example of such substances is n-dodecyl alcohol.

BRIEF DESCRIPTION OF THE DRAWINGS

FIG. 8 shows correlation to the conventional example, and FIGS. 7 and 9 show correlations to the embodiments of the present invention.

DETAILED DESCRIPTION OF THE PREFERRED EMBODIMENTS

Figure 1:
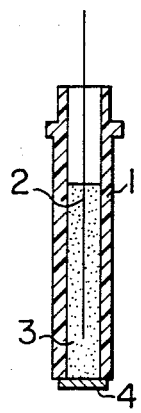
FIG. 1 is a schematic view showing the structure of an anion-selective electrode according to one embodiment of the present invention.

First of all, ion-sensitive substances relating to the present invention will be described below.

Quaternary ammonium salts can be classified in the following four types (quaternary phosphonium salts are substitutes of N with P in ammonium salts.

Type (1) 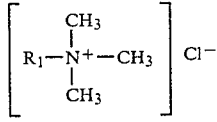

-continued

Type (2)
$$\left[\begin{array}{c} CH_3 \\ | \\ R_1-N^+-R_1 \\ | \\ CH_3 \end{array}\right] Cl^-$$

Type (3)
$$\left[\begin{array}{c} R_1 \\ | \\ R_1-N^+-CH_3 \\ | \\ R_1 \end{array}\right] Cl^-$$

Type (4)
$$\left[\begin{array}{c} R_1 \\ | \\ R_1-N^+-R_1 \\ | \\ R_1 \end{array}\right] Cl^-$$

where $R_1$ represents an aliphatic alkyl group having at least 8 carbon atoms.

The structures of the four types have the following characteristics: the lipophilicity of quaternary ammonium salts themselves is generally intensified with increasing number of $R_1$ groups. From the viewpoint of lipophilicity, compounds of type (1) have a poor lipophilicity, and if $R_1$ is smaller, the compounds are hard to use as the ion-sensitive substance, or even if used, they will be dissolved out of the film in a short time. If the compounds of type (1) have an $R_1$ group having at least 36 carbon atoms ($C_{36}$), their lipophilicity will be drastically intensified, and they can be practically used. However, such compounds are hard to synthesize and, if synthesized, are very expensive.

On the other hand, the lipophilicity of compounds of types (2), (3) and (4) can be readily intensified with increasing number of $R_1$ groups, even if the $R_1$ groups themselves have smaller number of carbon atoms. Particularly, compounds of type (4) can have a practically sufficient lipophilicity, even if each $R_1$ group has only 10 carbon atoms, because carbon atoms amount to 40 in total ($C_{40}$). From the foregoing it can be said that any compound other than type (1) has a practical possibility as the quaternary ammonium salt for the ion-sensitive substance.

According to a desirable mode of the present invention quaternary ammonium salts of dimethyldialkyl type of type (2) are used as the ion-sensitive substance, and those with dioctadecyl type as the carbon number in each $R_1$ group ($C_{18}$) are particularly preferable. If the $R_1$ group has less then $C_{16}$, the solubility of the compounds in water is increased, and thus the compounds are less practical. On the other hand, if the $R_1$ group has more than $C_{20}$, choice of plasticizer capable of dissolving the compounds and establishing a dissociated ionized state of (+) ions (ion-exchanging groups) and (−) ions (ion species to be measured) is largely limited. This is also true of compounds of types (3) and (4), where the number of carbon atoms in each $R_1$ group is only differentiated, that is, reduced.

Among the compounds of types (2), (3), and (4), dimethyldialkyl ammonium salts of type (2) with long alkyl chains have the best effect on measuring chloride ions, where alkyl groups each having 16-24 carbon atoms can be used. An appropriate content of dimethyldioctadecylammonium chloride dispersed in the sensitive film is 5-30% by weight from the viewpoint of responsiveness, selectivity and formability of the support film.

In the foregoing embodiment, n-tetradecyl alcohol is used as the plasticizer of low dielectric constant, but the plasticizer of low dielectric constant is not limited thereto. Linear alcohols with a good lipophilicity having at least 10 carbon atoms, particularly aliphatic alcohols, are suitable as the plasticizer of low dielectric constant. Particularly, aliphatic alcohols having 10-20 carbon atoms and a dielectric constant of not more than 10 have a good effect.

n-tetradecyl alcohol having a dielectric constant of about 4(20° C.) is in a crystalline form at room temperature (melting point: 38.3° C.), but has a low water solubility and a hydroxyl group (—OH group) in the molecular structure, and is very effective for reducing deposition or adsorption of protein behaving as an amphoteric ion onto the surface of a sensitive film. However it has been found from results of experiments that the effect of inhibiting protein deposition is based not only on the presence of the plasticizer of low dielectric constant, but also on a combination with other components. An appropriate content of n-tetradecyl alcohol in the sensitive film is 5-40% by weight.

When the tetradecyl alcohol is the only plasticizer in the sensitive film, the resulting liquid film type, anion-selective electrode fails to work normally, because dimethyldioctadecylammonium chloride as an anion-sensitive substance cannot be dissolved.

Another plasticizer must be contained in the sensitive film. When a liquid organic compound with a high lipophilicity having a dielectric constant of at least 15 is also contained as another plasticizer, a liquid film type, anion-selective electrode can work normally. As the plasticizer of high dielectric constant, cyclic compounds having at least 6 carbon atoms and aliphatic compounds having at least 10 carbon atoms, which are hardly dissolved out of the film into an aqueous solution, can be selected.

o-nitrophenyloctyl ether (which will be hereinafter referred to as o-NPOE) has a dielectric constant of about 24(25° C.). Such a substance of high dielectric constant can dissolve dimethyldioctadecylammonium chloride as an anion-sensitive substance in the sensitive film and also can occasion a reaction condition for shifting the equilibrium in an ion dissociation reaction represented by the following equation (1) toward the right side, that is, in the direction to complete dissociation of ion-exchanging group ($S^+$) and counter ion ($Cl^-$).

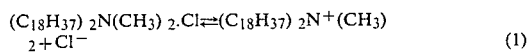

$$(C_{18}H_{37})_2N(CH_3)_2 \cdot Cl \rightleftharpoons (C_{18}H_{37})_2N^+(CH_3)_2 + Cl^- \quad (1)$$

At a liquid film type, anion-selective, electrode, it is essential for obtaining basic characteristics of an ion electrode that the ion-exchanging group ($S^+$) and counter ion ($Cl^-$) are dissolved (dissociated) to some extent, as shown by the above-mentioned reaction. By simultaneous presence of a plasticizer of low dielectric constant and a plasticizer of high dielectric constant, a good result of measurement for body fluid samples containing many components of various properties can be obtained with less disturbance by ionic substances with a high lipophilicity. An appropriate content of o-NPOE in the sensitive film is 5-30% by weight.

Nitrobenzene derivatives other than o-NPOE can be used as the plasticizer of high dielectric constant. For example, o-nitrotoluene (dielectric constant: about 27 at 20° C.), m-nitrotoluene (dielectric constant: about 23 at 20° C.), p-nitrotoluene (dielectric constant: about 22 at 58° C.), etc. have a high lipophilicity aand a low solubility in an aqueous solution. In addition, nitrobenzene (dielectric constant: about 35 at 25° C.), acetophenone derivatives, etc. can be also used as the plasticizer of high dielectric constant.

Figure 2:
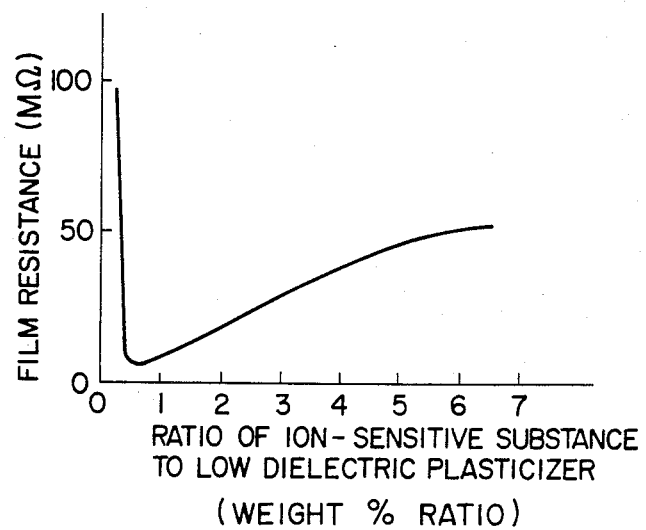
FIG. 2 is a diagram showing relationships between the content ratio of ion-sensitive substance to plasticizer, and the film resistance.

In FIG. 2, relationships between the ratio of ion-sensitive substance to n-tetradecyl alcohol as a plasticizer of low dielectric constant, and the electrode film resistance, are shown, where dimethyldioctadecylammonium chloride is used as an ion-sensitive substance and the contents of o-NPOE as the plasticizer of high dielectric constant and polyvinyl chloride as a support film material are fixed at 10% by weight and 50% by weight, respectively.

As shown in FIG. 2, when the ratio of ion-sensitive substance (dimethyldioctadecylammonium chloride) to plasticizer of low dielectric constant (n-tetradecyl alcohol) is less than 0.4 by weight % ratio, the film resistance increases drastically. Generally, it is desirable that the ion-sensitive film as a sensor has a film resistance as low as possible (less than about 50 M$\Omega$). This is very important from the viewpoint of easy pickup of induction noise or faster response time. In this sense, it is seen from FIG. 2 that a preferable ratio of an anion-sensitive substance to n-tetradecyl alcohol is in a range of about 0.4 to about 5 by weight % ratio. This range is practically preferable also from the viewpoint of film preparation and less crystallization of the ion-sensitive substance or plasticizers.

Support film material for the sensitive substance and plasticizers will be described below.

Polyvinyl chloride, epoxy resin, silicone resin, cellulose resin, etc. are practically applicable as polymer resins for the support film material. Particularly, polyvinyl chloride is suitable for body fluid samples such as serum, etc., and is also more advantageous from the viewpoint of not only processability, but also applicability of various plasticizers, than other support film materials.

Figure 3:
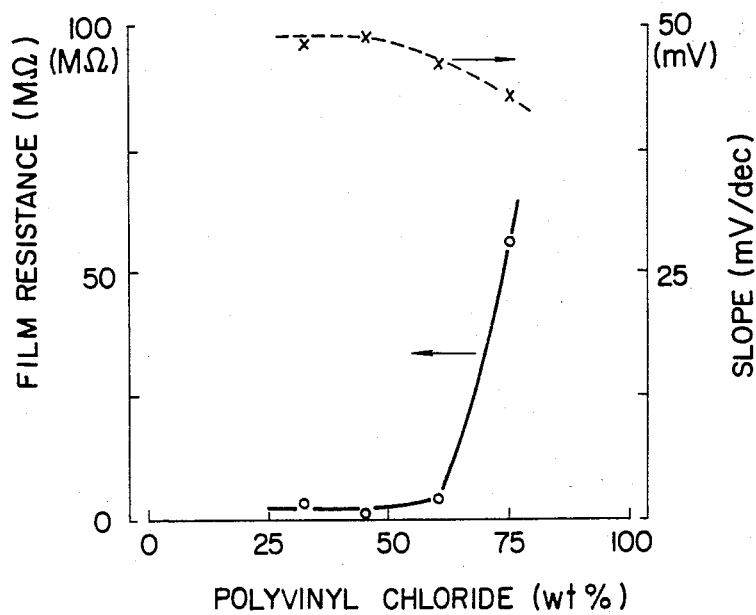
FIG. 3 is a diagram showing relationships between the content of polyvinyl chloride and the film resistance or the slope.

In FIG. 3, relationships between the film resistance (full line) of the ion-sensitive film and the slope (dotted line) are shown when the content of polyvinyl chloride (% by weight) is changed while keeping the ratio of ion-sensitive substance to n-tetradecyl alcohol at 1:2 by weight % ratio, where the slope is a gradient defined by Nernst equation relating an electrode electromotive force to an ion activity. The Nernst equation is given as follows:

$$E = Eo \pm S \log a$$

where
E: electromotive force
Eo: value determined by a measuring system
a: ionic activity of ion to be measured
S: a difference in electromotive force when the ionic activity is changed by one digit, i.e. slope As is obvious from FIG. 3, it is preferable that the content of polyvinyl chloride is not more than about 70% by weight where the film resistance is below 50 M$\Omega$. With that content of polyvinyl chloride, the slope is also large, and thus a stable electromotive force can be obtained. When the content of polyvinyl chloride is below 25% by weight, the mechanical strength of the sensitive film becomes very low owing to other components involved, and the function as the film becomes poor. Thus an appropriate content of polyvinyl choride is 25–70% by weight.

Figure 4:
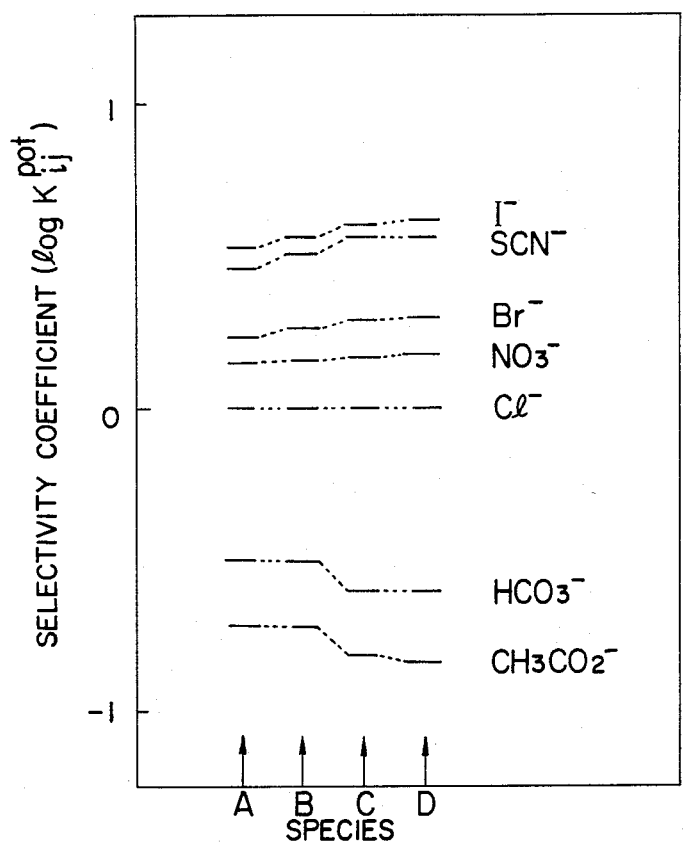
FIG. 4 is a diagram showing selectivity coefficients of a chloride ion-selective electrode according to the present invention for various species of anions.

In FIG. 4, selectivity coefficients to various anions on the basis of chloride ion are shown for 4 species of anion-selective electrodes with different polyvinyl chloride contents, prepared in the same manner as in FIG. 3. Polyvinyl chloride content is 75% by weight for species A, 60% by weight for species B, 45% by weight for species C and 30% by weight for species D. The selectivity coefficient is obtained by a single solution method. From FIG. 4, it is difficult to judge which film is most practical, and particularly more difficult with a sample containing much lipophilic components and bicarbonate ions as hydrophilic anions at the same time, such as serum. In view of a change in time of the film, that is, a possibility of dissolving the ion-sensitive substance and plasticizers from the film, a film having higher contents of ion-sensitive substance and plasticizers is more stable for a long time. Example 1

In FIG. 1, one embodiment of the present invention is shown, where an internal electrolyte 3 is stored in a cylindrical body 1 of polyvinyl chloride, and an internal electrode (Ag/AgCl) 2 is dipped in the internal electrolyte 3, while a liquid film type, anion-sensitive film 4 is formed at one end of the body 1.

The ion-sensitive film 4 is prepared in the following manner:

10% by weight of dimethyldiotadecylammonium chloride as an anion-sensitive substance, 30% by weight of n-tetradecylalcohol having a dielectric constant of about 4 as a plasticizer of low dielectric constant, 10% by weight of o-nitrophenyloctylether having a dielectric constant of about 24 as a plasticizer of high dielectric constant, and 50% by weight of polyvinyl chloride as a film support material are mixed and dissolved in a solvent such as tetrahydrofuran, cyclohexanone or the like. The resulting solution is poured into a mold of definite shape, and the solvent is removed by evaporation to obtain a sheet of sensitive film for chloride ions. The sheet is cut into a disc form corresponding to the size of body 1 of FIG. 1, and then bonded to the end of body 1. In the sensitive film, the plasticizer of low dielectric constant, the plasticizer of high dielectric constant, and the anion-sensitive substance are uniformly dispersed in the support film material.

Then, an aqueous sodium chloride (NaCl) solution with a concentration of $10^{-2}$ M is poured into the body 1 as internal electrolyte 3. Then, a silver/silver chloride wire is dipped into the internal electrolyte 3 as the internal electrode 2. The internal electrode 2 is connected to an amplifier (not shown on the drawing). The thus prepared anion-selective electrode is dipped in a sample liquid together with a reference electrode connected to the amplifier, and a generated electromotive force is measured to determine a chloride ion concentration.

In this example, the quaternary ammonium salt is used as the anion-sensitive substance, and a quaternary phosphonium salt can be dispersed and supported in the sensitive film in place of the ammonium salt.

EXAMPLE 2

As a composition for the sensitive film of FIG. 1, 15% by weight of dimethyldioctadecylammonium chloride, 30% by weight of n-tetradecyl alcohol, 10% by weight of o-nitrophenyloctylether, and 45% by weight of polyvinyl chloride are mixed and dissolved in tetrahydrofuran, and a sensitive film is prepared therefrom in the same manner as in Example 1 and fixed to the electrode body.

EXAMPLE 3

As a composition for the sensitive film of Example 1, 10% by weight of dimethyldioctadecylammonium chloride, 30% by weight of n-tetradecyl alcohol, 10% by weight of o-NPOE, 2% by weight of n-dodecyl alcohol and 48% by weight of polyvinyl alcohol are mixed and dissolved in tetrahydrofuran. Then, a sensitive film is prepared therefrom in the same manner as in Example 1, and fixed to the electrode body. n-dodecyl alcohol can increase the solubility of anion-sensitive substances and reduce the crystallization of other plasticizers. An appropriate content of this third plasticizer is 1-10% by weight.

EXAMPLE 4

A solution A is prepared by dissolving an anion-sensitive substance, a plasticizer of low dielectric constant and a support film material in a solvent. A solution B is prepared by dissolving an anion-sensitive substance, a plasticizer of high dielectric constant and a support film material in a solvent (tetrahydrofuran). At first, the solution A is applied to a flat plate, and the solvent is evaporated off to form a film. Then, the solution B is applied to the thus obtained film, and the solvent is evaporated off to form a film as the second layer. Thereafter, the solutions A and B are alternately applied one after another and dried to obtain a multi-layer film. The thus obtained multi-layer film is cut into a disc form, and bonded to one end of the electrode body as in FIG. 1. The anion-sensitive film consisting of such a multi-layer film contains both the plasticizer of high dielectric constant and the plasticizer of low dielectric constant.

In this example, the solutions A and B are applied alternately, but an electrode body itself can be dipped in the solutions A and B alternately, and dried to obtain a multi-layer, anion-sensitive film.

Effect of embodiments according to the present invention will be described below.

For comparison of the present invention, two examples of prior art are given below. A first example of prior art is a modification of an anion-selective electrode shown in Japanese Patent Application Kokai (Laid-open) No. 57-77952, where the sensitive film contains 15% by weight of methyltridodecylammonium chloride as a sensitive substance, 30% by weight of n-tetradecyl alcohol as a single plasticizer, and 55% by weight of polyvinyl chloride as a support film material. A second example of prior art is based on an anion-selective electrode disclosed in Japanese Patent Application Kokai (Laid-open) No. 54-89689, where the sensitive film contains 15% by weight of methyltridodecylammonium chloride as a sensitive substance, 15% by weight of o-nitrophenyl-octylether as a single plasticizer, and 70% by weight of polyvinyl chloride as a support film material.

Figure 5:
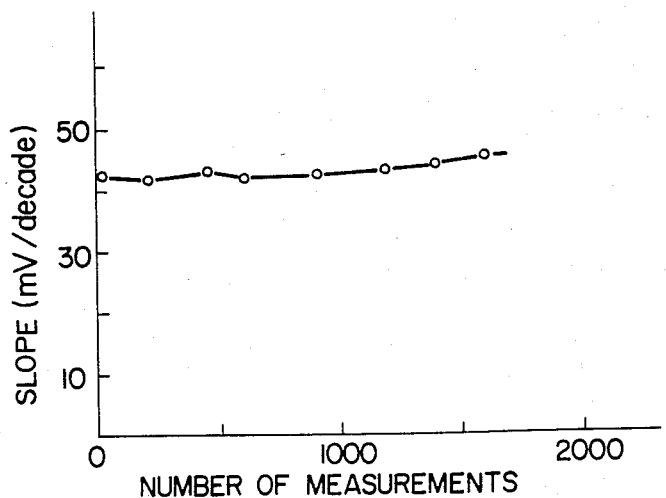
FIG. 5 is a diagram showing changes in slope of a chloride ion-selective electrode according to the present invention when applied to measurement of human serum.

In FIG. 5, are shown changes in slope when about 1,600 samples of human serum were investigated with the electrode of Example 1. It is obvious from FIG. 5 that the change in slope is very small and thus the electrode has a long life. As a result of observation of the sensitive film surface after the measurement of serum, no substantial deposition of protein is observed, which seems to lead to the very small change in slope to produce a high stability for a long time. For example, the number of possible measurements of serum samples according to the first example of prior art is limited to 1,000, and that according to the second example of the prior art the number of possible measurements is much smaller, that is, the life is shorter.

Figure 6:
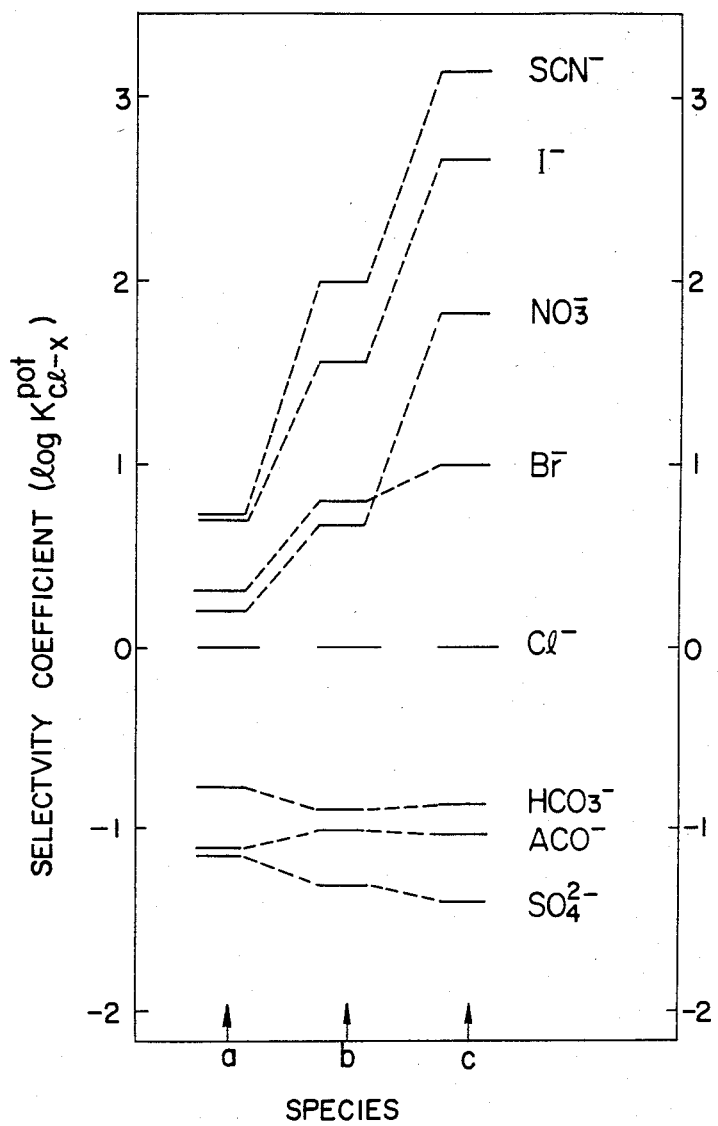
FIG. 6 is a diagram showing results of measuring selectivity coefficients of a chloride ion-sensitive electrode according to the present invention, and the conventional chloride ion-selective electrode, for various species of anions.

In FIG. 6 are shown results of measuring selectivity coefficients to various ion species, based on the chloride ion, by the electrode of Example 2 and the electrode of the first and second examples of prior art, where a shows the results by Example 2 of the present invention, b those by the first example of prior art, and c those by the second example of prior art.

As is obvious from FIG. 6, the electrode of the present invention has no remarkable improvement in selectivity to hydrophilic anions such as acetate ion ($CH_3CO_2^-$), etc., as compared with the prior art electrodes, but has a remarkable improvement in selectivity to anions of high lipophilicity such as thiocyanate ions ($SCN^-$), etc.

Figure 7:
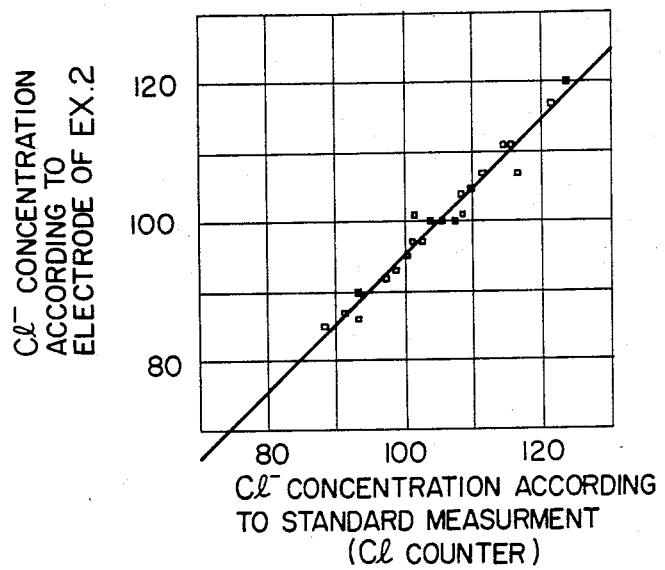
FIGS. 7-9 are diagrams showing correlations to coulometry when commercially available, controlled serum is used, where

In FIG. 7 is shown a correlation between measurements of chloride ion concentration of 22 species of commercially available, controlled serum by the electrode of Example 2 containing two kinds of plasticizers (shown on the ordinate) and those by the standard method (shown on the abscissa). The standard method for the abscissa values is a coulometry method utilized as a method for stable measurement, though requiring much time.

Figure 8:
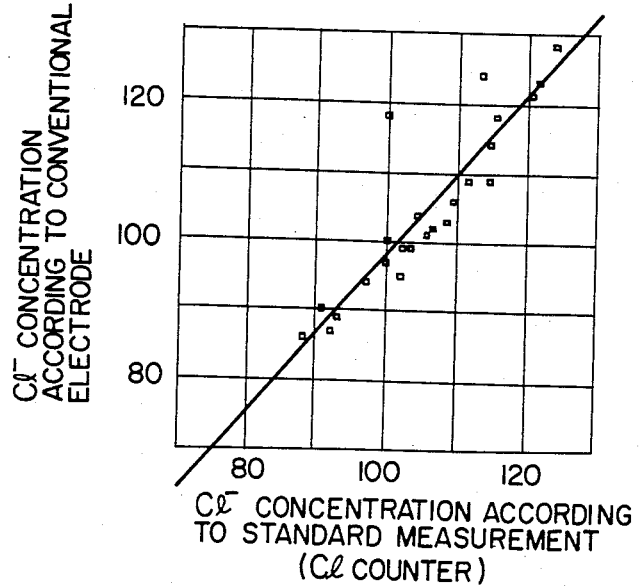

For comparison, in FIG. 8 is shown a correlation between the $Cl^-$ measurements of 24 species of the controlled serum by the first example of the prior art and those by the coulometry as the standard method. It is seen from FIG. 7 and FIG. 8 that a better correlation can be obtained with a smaller error of measurement according to the present invention (FIG. 7).

Figure 9:
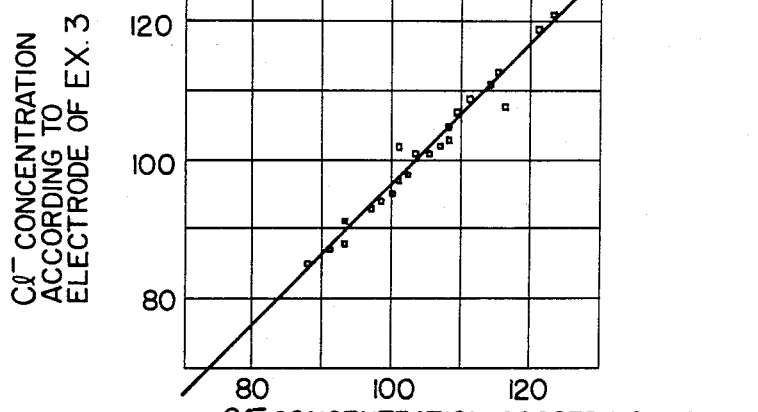

In FIG. 9 is shown a similar correlation of $Cl^-$ measurements of 22 species of the controlled serum by the electrode of Example 3 containing three kinds of plasticizers according to the present invention. A much better correlation can be obtained than FIG. 7.

The measurement according to the examples according to the present invention has a good correlation to the standard method, and the present anion-selective electrode has less deposition of protein, etc. and a high selectivity, and has a response speed at least twice that of the first example of the prior art. Thus, the present invention provides a very practical liquid film type, anion-selective electrode.

According to the present invention, a selectivity can be improved and deposition of protein, etc. can be reduced by adding to an anion-sensitive film both a plasticizer of high dielectric constant and a plasticizer of low dielectric constant, and thus measurements with small errors of measurement can be effectively obtained.

What is claimed is:

1. A liquid film type, anion-selective electrode comprising a sensitive film containing polymer resin as a support film material, a quaternary ammonium salt or a quaternary phosphonium salt as an anion-sensitive substance, at least 5% by weight of a linear alcohol having a dielectric constant of not more than 10 and at least 5% by weight of an organic compound having a dielectric constant of not less than 15.

2. A liquid film type, anion-selective electrode according to claim 1, wherein the quaternary ammonium salt is a compound having a plurality of aliphatic alkyl groups, sum total of carbon atoms in the alkyl groups being at least 32.

3. A liquid film type, anion-selective electrode according to claim 1, wherein a ratio of the anion-sensitive substance to the linear alcohol is 0.4-5 by weight % ratio.

4. A liquid film type, anion-selective electrode according to claim 1, wherein the compound of high dielectric constant is o-nitrophenyloctylether, and its content is 5-30% by weight.

5. A liquid film type, anion-selective electrode according to claim 1, wherein the linear alcohol is n-tetradecyl alcohol and its content is 5-40% by weight.

6. A liquid film type, anion-selective electrode according to claim 1, wherein the content of the support film material is 25-70% by weight.

7. A liquid film type, anion-selective electrode according to claim 1, wherein the anion-sensitive substance is dimethyl-di-alkylammonium salt with the alkyl groups each having 16-24 carbon atoms.

8. A liquid film type, anion-selective electrode according to claim 7, wherein the content of the dimethyl-dialkylammonium salt in the sensitive film is 5-30% by weight.

9. A liquid film type, anion-selective electrode according to claim 1, wherein the plasticizer of low dielectric constant and the plasticizer of high dielectric constant are uniformly dispersed in the support film material.

10. A liquid film type, anion-selective electrode according to claim 1, wherein the sensitive film is a film consisting of first layers containing the plasticizer of low dielectric constant and the anion-sensitive substance and second layers containing the plasticizer of high dielectric constant and the anion-sensitive substance, the first layers and the second layers being alternately arranged one upon another.

11. A liquid film type, anion-selective electrode according to claim 1, wherein said linear alcohol has at least 10 carbon atoms.

12. A liquid film type, anion-selective electrode according to claim 11, wherein said linear alcohol has 10-20 carbon atoms.

13. A liquid film type, anion-selective electrode according to claim 12, wherein said organic compound is a cyclic compound, and has at least 6 carbon atoms.

14. A liquid film type, anion-selective electrode according to claim 12, wherein said organic compound is an aliphatic compound, and has at least 10 carbon atoms.

15. A liquid film type, anion-selective electrode according to claim 1, wherein said anion-sensitive substance is a quaternary ammonium salt having a plurality of aliphatic alkyl groups, the sum total of the carbon atoms of the alkyl groups being at least 32.

16. A liquid film type, anion-selective electrode according to claim 15, wherein said support film material is polyvinyl chloride.

17. A liquid film type, anion-selective electrode according to claim 16, wherein said support film material is used in an amount of 25-70% by weight.

18. A liquid film type, anion-selective electrode according to claim 1, wherein said organic compound is selected from the group consisting of o-nitrotoluene, m-nitrotoluene, p-nitrotoluene, nitrobenzene and acetophenone derivatives.

19. An anion-selective electrode, which comprises a sensitive film containing polymer resin as a support film material, a quaternary ammonium salt or a quaternary phosphonium salt as an anion-sensitive substance, at least 5% by weight of a linear alcohol having a dielectric constant of not more than 10, at least 5% by weight of an organic compound having a dielectric constant of not less than 15, and a substance dissolving the anion-sensitive substance.

20. An anion-selective electrode according to claim 19, wherein the substance dissolving the anion-sensitive substance is n-dodecyl alcohol.

21. An anion-selective electrode according to claim 20, wherein the content of the n-dodecyl alcohol is 1-10% by weight.

22. A liquid film type, anion-selective electrode containing polymer resin as a support film material, a quaternary ammonium salt or a quaternary phosphonium salt as an anion-sensitive substance, linear alcohol having a dielectric constant of not more than 10, and an organic compound having a dielectric constant of not less than 15, the amounts each of the linear alcohol and the organic compound being effective amounts such that deposition of proteins on said sensitive film can be reduced, as compared to a film comtaining no linear alcohol, while providing for dissolving of the anion-sensitive substance.

23. A liquid film type, anion-selective electrode according to claim 22, wherein each of said linear alcohol and organic compound are lipophilic compounds.

24. A liquid film type, anion-selective electrode according to claim 23, wherein each of said linear alcohol and organic compound are substantially water-insoluble.

25. A liquid film type, anion-selective electrode comprising a sensitive film containing polymer resin as a support film material, a quaternary ammonium salt or a quaternary phosphonium salt as an anion-sensitive substance, a linear alcohol having a low dielectric constant, and an organic compound having a dielectric constant higher than that of said linear alcohol, the linear alcohol and organic compound having dielectric constants, and being contained in the film in amounts, effective such that deposition of proteins on said sensitive film is reduced, as compared to a film containing no linear alcohol, while providing for dissolving of the anion-sensitive substance.

26. A liquid film type, anion-selective electrode according to claim 25, wherein said organic compound has a dielectric constant of at least 15.

27. A liquid film type, anion-selective electrode according to claim 26, wherein each of said linear alcohol and organic compound are lipophilic compounds.

28. A liquid film type, anion-selective electrode according to claim 27, wherein said linear alcohol has at least 10 carbon atoms.

* * * * *